United States Patent
Koyanagi

(10) Patent No.: US 6,509,200 B2
(45) Date of Patent: Jan. 21, 2003

(54) METHOD OF APPRAISING A DIELECTRIC FILM, METHOD OF CALIBRATING TEMPERATURE OF A HEAT TREATMENT DEVICE, AND METHOD OF FABRICATING A SEMICONDUCTOR MEMORY DEVICE

(75) Inventor: Kenichi Koyanagi, Tokyo (JP)

(73) Assignees: NEC Corporation, Tokyo (JP); Hitachi, Ltd., Tokyo (JP)

( * ) Notice: Subject to any disclaimer, the term of this patent is extended or adjusted under 35 U.S.C. 154(b) by 0 days.

(21) Appl. No.: 10/083,612

(22) Filed: Feb. 27, 2002

(65) Prior Publication Data

US 2002/0137239 A1 Sep. 26, 2002

(30) Foreign Application Priority Data

Mar. 26, 2001 (JP) .................................... 2001-086662

(51) Int. Cl.[7] .............................................. H01L 21/66
(52) U.S. Cl. ............................ 438/14; 438/16; 438/18
(58) Field of Search ........................... 438/14, 15, 16, 438/18; 428/688, 328

(56) References Cited

U.S. PATENT DOCUMENTS

| | | | | |
|---|---|---|---|---|
| 3,925,221 A | * | 12/1975 | Eustance | .................... 252/574 |
| 4,877,988 A | * | 10/1989 | McGinniss et al. | .......... 310/306 |
| 5,563,182 A | * | 10/1996 | Epstein et al. | ............... 522/146 |
| 5,663,255 A | * | 9/1997 | Anolick et al. | .............. 526/254 |
| 6,010,538 A | * | 1/2000 | Sun et al. | ............... 156/345.13 |
| 6,326,090 B1 | * | 12/2001 | Schultz et al. | ............... 428/688 |
| 6,432,526 B1 | * | 8/2002 | Arney et al. | ................ 428/328 |
| 6,437,506 B1 | * | 8/2002 | Mitamura et al. | ........... 313/586 |

* cited by examiner

Primary Examiner—John F. Niebling
Assistant Examiner—Olivia Luk
(74) Attorney, Agent, or Firm—Young & Thompson

(57) ABSTRACT

When tantalum pentoxide film that is deposited on silicon wafer is subjected to a heat treatment in an oxygen atmosphere to improve crystallinity, refractive index is measured by an ellipsometer to appraise change in the crystallinity or change in the relative dielectric constant of the dielectric film and judge the adequacy of the heat treatment temperature. In particular, when the dielectric film is a structure that includes tantalum pentoxide film in which crystallinity is changed by heat treatment and silicon oxide film in which film thickness is changed by heat treatment, the temperature of the heat treatment can be accurately appraised by taking advantage of the correlation between the temperatures of the heat treatment and the refractive indices of the laminated films, this correlation having a curve with a maximum point and a minimum point.

19 Claims, 8 Drawing Sheets

METHOD OF APPRAISING A DIELECTRIC FILM, METHOD OF CALIBRATING TEMPERATURE OF A HEAT TREATMENT DEVICE, AND METHOD OF FABRICATING A SEMICONDUCTOR MEMORY DEVICE

BACKGROUND OF THE INVENTION

1. Field of the Invention

The present invention relates to a method of appraising a dielectric film, a method of calibrating the temperature of a heat treatment device, and a method of fabricating a semiconductor memory device; and in particular, to an ideal method of appraising a dielectric film, this appraisal in turn being used to appraise the crystallinity of a dielectric film that is grown on a DRAM capacitor; a method of calibrating the temperature of a heat treatment device; and a method of fabricating a semiconductor memory device.

2. Description of the Related Art

In recent years, the development of large-capacity memory elements has been advancing with the development of semiconductor fabrication technology. The progress toward higher integration of DRAM (Dynamic Random Access Memory) in which one memory cell is constituted by a single capacitor and a single transistor has been particularly rapid. Although capacitors of higher capacitance are required in order to maintain reliability such as resistance to soft errors in semiconductor memory devices such as DRAM, the area that can be occupied by capacitors is decreasing as semiconductor memory device become more highly integrated.

Since the charge storage capacity of a capacitor increases in proportion to the electrode area of the capacitor and the dielectric constant of the dielectric film and in reverse proportion to the thickness of the dielectric film, various methods have been proposed for increasing the electrode area of capacitors. Known methods include methods in which the (storage node) electrodes themselves are processed to a fin shape or crown shape, or methods in which HSG (Hemi-Spherical Grains) are formed.

As a simplified explanation of this HSG formation mechanism, when an amorphous silicon film having a clean surface is heated to a temperature sufficient to cause crystallization, the silicon atoms are dispersed within the film with high mobility, and collisions between these silicon atoms result in the formation of crystal nuclei. Crystallization centering on these crystal nuclei progresses from the surface of the film in the direction of depth of the film, and hemispherical crystals having a diameter of several tens of nanometers are formed, thereby producing a minute roughness is produced on the surface.

The use of this HSG technique enables the formation of capacitors having more than twice the surface area of a flat surface.

Alternatively, as methods of increasing the capacitance of a capacitor without changing the electrode area, research is in progress both regarding the reduction of the thickness of the dielectric film and regarding dielectric films that have a high relative dielectric constant. In recent years, tantalum pentoxide ($Ta_2O_5$), yttrium oxide ($Y_2O_3$), and hafnium dioxide ($HfO_2$) are receiving attention as films having a high dielectric constant. These materials have a relative dielectric constant that is markedly higher than a silicon oxide film, which has a relative dielectric constant of 3–4, or a silicon nitride film, which has a relative dielectric constant of 6–8.

Tantalum pentoxide, which is a material having inherent-thermodynamic stability, is particularly promising as a material for DRAM capacitors.

Tantalum pentoxide has a relative dielectric constant on the order of 22–25 even as a thin film, and a film can therefore be grown by sputtering, CVD (Chemical Vapor Deposition), or sol-gel. After formation of the tantalum pentoxide film, the tantalum pentoxide is next subjected to a heat treatment in an oxygen atmosphere to raise the relative dielectric constant to approximately 40. The chief objective of this heat treatment is to improve the crystallinity of the tantalum pentoxide film, and the treatment is carried out in an oxygen atmosphere to maintain the crystallinity of the tantalum pentoxide film.

Thus, an increase in the capacitance of the capacitors is achieved by: forming HSG on the capacitors of a semiconductor memory device such as DRAM to increase the surface area, growing a film of a material having a high dielectric constant such as tantalum pentoxide on this roughened surface, and then subjecting the surface to a heat treatment. In a DRAM fabrication method that employs this tantalum pentoxide film, however, there is the problem that the effect of the heat treatment on the tantalum pentoxide film cannot be adequately judged.

If the area of the electrode is fixed as described above, the electrostatic capacity of the capacitors varies depending on the relative dielectric constant and film thickness of the-dielectric film. Although reproducibility of the film thickness of the dielectric film can be secured by adjusting the conditions of the CVD film-forming device, the dielectric constant of the dielectric film varies depending on the crystallinity of the dielectric film itself, and therefore varies greatly according to the temperature condition of the heat treatment.

This problem is further explained with reference to FIG. 3, which shows the correlation between the temperature (RTO temperature) of the heat treatment and the refractive index of the dielectric film. As shown in FIG. 3A, the refractive index, which indicates the crystallinity of the dielectric film, does not gradually increase with increase in the temperature of the heat treatment, but rather, changes abruptly with a particular temperature as a line of demarcation and then increases to a fixed value. This phenomenon occurs due to a rapid improvement in the crystallinity of the tantalum pentoxide from an amorphous state to a crystalline state when the heat energy exceeds a particular threshold value, and after this improvement in crystallinity, density does not change despite further increase in temperature.

Accordingly, to improve the crystallinity of a dielectric film and set the dielectric constant to a desired value, the temperature of the heat treatment is preferably set as high as possible. However, components such as transistors are formed in layers below the capacitors of a semiconductor memory device, and setting the temperature of the heat treatment to a high level results in problems such as change in the distribution of impurity concentration in diffusion layers and the alteration of the characteristics of transistors due to the diffusion of impurities into unintended areas. Thus, when actually fabricating a semiconductor memory device such as DRAM, the temperature of the heat treatment is preferably set to the vicinity of the border between area II and area II in FIG. 3A. Since this is an area in which the refractive index changes rapidly with respect to change in temperature, the temperature of the heat treatment must be: set accurately.

In semiconductor fabrication devices such as heat treatment devices, the treatment temperature is typically controlled based on the indication of a temperature sensor that is installed inside the device, but factors such as the position of installation of the temperature sensor inside the device or the shape and amount of the sample that is being used may result in divergence between the temperature that is indicated on the device and the actual treatment temperature. This divergence may further vary over time according to factors such as the operation time of the device.

In order to correct this divergence in temperature, a method may be adopted in which a sample for temperature calibration on which a dielectric film has been grown is used to actually carry out the heat treatment, following which the crystallinity of the dielectric film after the heat treatment is then appraised by, for example, an x-ray diffraction method to estimate the actual treatment temperature and adjust the set temperature of the device. However, this approach is problematic both because the x-ray diffraction method takes time to perform and because a correspondence cannot be established between the x-ray diffraction data and the treatment temperature after the crystallinity of the dielectric film has been improved, whereby calibration data cannot be obtained for the vicinity of the point of inflection that is of utmost important in the heat treatment device.

In addition, when using the above-described x-ray diffraction method to appraise a dielectric film in an actual fabrication process of DRAM, a wafer product cannot be used in appraisal because x-rays are emitted in the x-ray diffraction method, and further, the appraisal depends on the underlying constituent substances. It is therefore necessary to place a dummy wafer for measurement purposes inside the film-forming device when growing the dielectric film and subject the dummy wafer to an oxidation treatment at the same time as the fabricated product to produce a sample for measurement purposes, and this requirement entails extra production steps. Even so, the dummy wafer will not necessarily be identical to the actual product due to differences in pattern and the state of the rear surface.

Furthermore, although the crystallinity of the dielectric film that is formed on the uppermost layer of the sample for measurement can be determined by the above-described x-ray diffraction method, the capacitance of the capacitors in an actual DRAM is reflected by the dielectric constant of not only the dielectric film of the uppermost layer, but of the entirety of laminated films that include the silicon oxide film, silicon nitride film, and polysilicon that are formed below the uppermost layer, and appraisal by x-ray diffraction therefore does not appraise the capacitance of the capacitors. In particular, oxygen atoms penetrate the dielectric film during the oxidation treatment and reach the silicon wafer, where a silicon oxide film forms on the silicon wafer interface; and the capacitance of the DRAM as a fabricated product cannot be accurately gauged if the dielectric constant of this entirety of laminated films is not measured.

Thus, there is the problem that, although an improvement in the surface area of the capacitance electrode, an improvement in the relative dielectric constant, and an increase in capacitance can be contrived by adopting an HSG construction for capacitors and by using a tantalum pentoxide film for the dielectric film, the lack of an effective means of measuring the total relative dielectric constant of the dielectric films in the capacitor means that the electrostatic capacitance of capacitors cannot be obtained with accuracy until an actual DRAM has been completed.

SUMMARY OF THE INVENTION

The present invention was achieved in view of the above-described problems and has as a first object the provision of a method of appraising dielectric films that enables easy and reliable estimation of the crystallinity or relative dielectric constant of a dielectric film, and in particular, laminated dielectric films without need for providing a dummy wafer.

It is a second object of the present invention to provide a method of calibrating the temperature of a heat treatment device that enables accurate correction of: divergence between a set temperature and the actual treatment temperature in a heat treatment device; divergence between the treatment temperatures of different devices; and fluctuation over time in the treatment temperature of individual devices.

It is a third object of the present invention to provide a method of fabricating a semiconductor memory device that, following heat treatment of a dielectric film, enables accurate estimation of the performance of DRAM capacitors as a fabricated product.

To achieve the above-described objects, the method of appraising dielectric films in the present invention is a method of appraising dielectric films that are deposited on a substrate; wherein at least one of change in the crystallinity and change in the relative dielectric constant of the dielectric film before and after a heat treatment that is performed in an atmosphere that contains oxygen is appraised by measuring the refractive index of the dielectric films.

In the present invention, the dielectric films can be composed of laminated films of a plurality of dielectric films each having different relative dielectric constants, and the invention can be constituted such that the refractive index of the laminated films is measured to estimate the refractive index of the entirety of the plurality of dielectric films.

The present invention may further be constituted such that the plurality of dielectric films includes: a dielectric film in which crystallinity is changed by the heat treatment, and a dielectric film in which film thickness is changed by the heat treatment.

In addition, the present invention may be constituted such that: the dielectric films preferably include any one of a tantalum pentoxide film, an yttrium oxide film, and a hafnium oxide film; the dielectric films are formed on silicon or a polysilicon film either in direct contact with the silicon or polysilicon film or with a silicon oxide film or silicon nitride film interposed, and a silicon oxide film is formed by the heat treatment at the interface of the silicon or the polysilicon film.

In the present invention, the refractive index is preferably measured by a spectral ellipsometer.

The present invention is a method of calibrating the temperature of a heat treatment device that subjects a dielectric film that has been deposited on a substrate to a heat treatment in an atmosphere that contains oxygen, wherein correlative data of the temperatures of the heat treatment and the refractive indices of the dielectric film that has undergone heat treatment at these temperatures are used to correct divergence between the set temperature of the heat treatment device and the actual treatment temperature.

The present invention may be constituted such that correlative data of the refractive indices of the dielectric films and the heat treatment temperatures that are obtained for each individual device of a plurality of the heat treatment devices are consulted to correct temperature differences between the plurality of heat treatment devices.

In addition, the present invention can be constituted such that correlative data of the temperatures of heat treatment and the refractive indices of dielectric films are obtained in advance for the heat treatment device, and the correlative data are then compared with data of the refractive index of a dielectric film that is subsequently subjected to treatment to correct for temperature fluctuation of the heat treatment device that occurs over time.

Still further, the present invention is a method of fabricating a semiconductor memory device that includes a step of carrying out a heat treatment in an atmosphere that contains oxygen after forming a dielectric film in capacitors; the step of subjecting the dielectric film to a heat treatment including using a portion of the substrate on which the semiconductor memory device is formed to measure, the refractive index of the dielectric film after the heat treatment to appraise at least one of: change in the crystallinity and change in the relative dielectric constant of the dielectric film, whereby the capacitance of the capacitors following completion of the semiconductor memory device is estimated.

In the present invention, a scribe line of the semiconductor memory device is preferably used for measuring the refractive index.

According to the constitution of the present invention, measurement of the refractive index of a dielectric film following an oxidation treatment enables measurement of, not only the crystallinity of the uppermost dielectric film, but the refractive index of the entirety of laminated films including a film that is formed at the interface, and thus enables an easy and reliable estimate of the capacitance of capacitors at a stage midway in fabrication. In addition, measurement in advance of correlative data of the refractive indices and heat treatment temperatures for each device enables detection of variations in the treatment temperatures between devices or of fluctuation in a device over time, and feedback of the results of comparing the correlative data with refractive indices that are measured after the heat treatment allows heat treatment devices to be kept in a uniform state. Furthermore, using a portion (such as a scribe line) of a semiconductor memory device such as DRAM to measure the refractive index enables measurement of the refractive index of a dielectric film that has been grown on an actual wafer product and allows accurate prediction of the cell capacitance of the semiconductor memory device.

The above and other objects, features, and advantages of the present invention will become apparent from the following description based on the accompanying drawings, which illustrate an example of a preferred embodiment of the present invention.

DETAILED DESCRIPTION OF THE PREFERRED EMBODIMENT

We now refer to the accompanying drawings to explain referred working examples of the present invention.

First Working Example

Figure 2A:
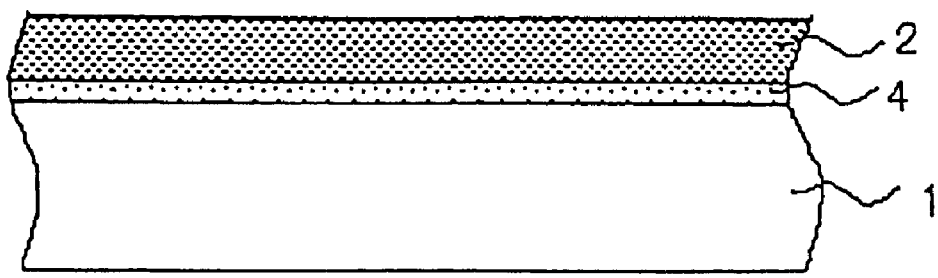
FIGS. 2A, 2B, and 2C are sectional views showing another construction of samples used in appraising a dielectric film according to the first working example of the present invention.
Figure 2B:
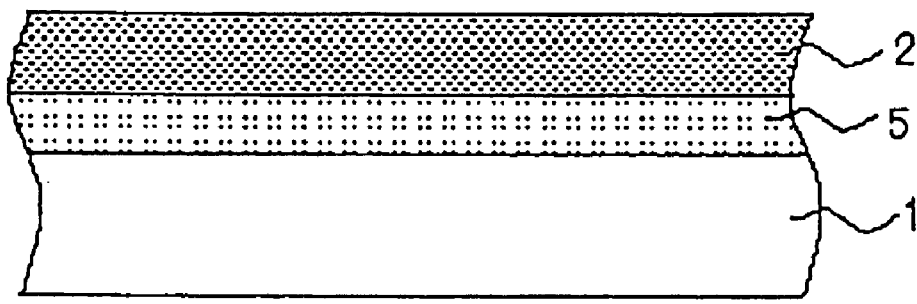
Figure 2C:
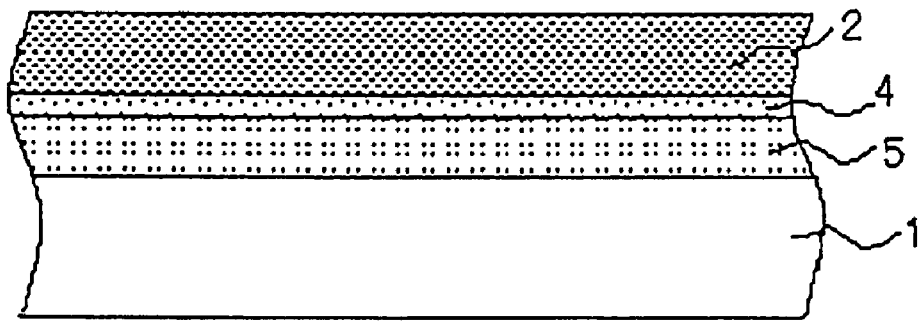
Figure 3A:
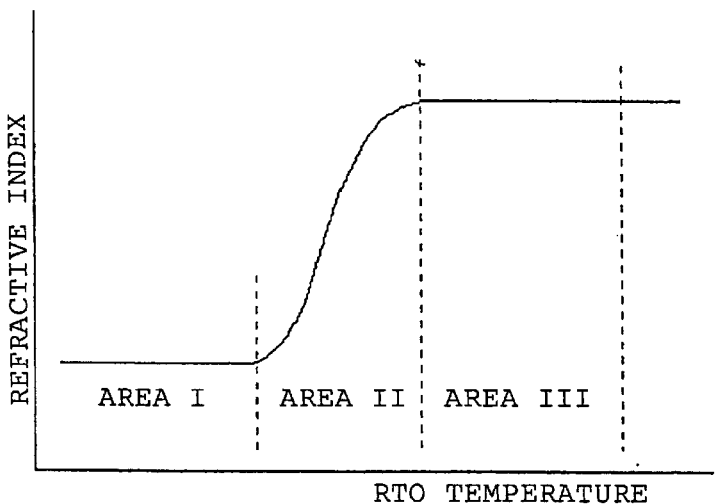
FIGS. 3A, 3B, and 3C are views for explaining the principles of the method of appraising a dielectric film according to the first working example of the present invention.
Figure 3B:
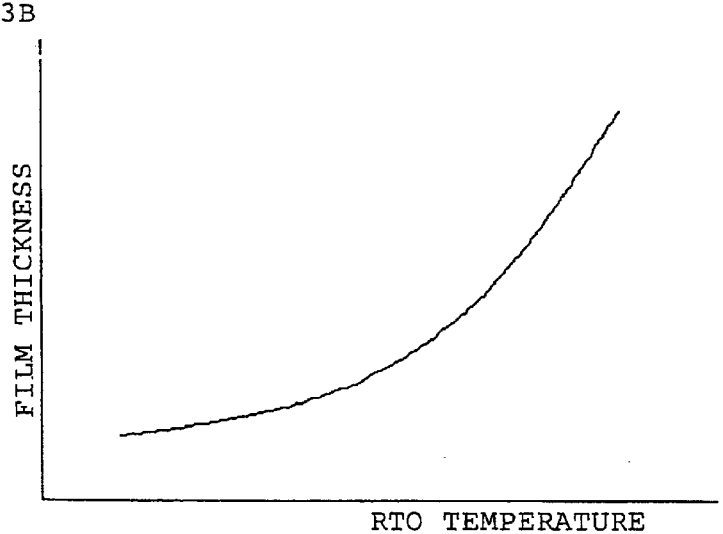
Figure 3C:
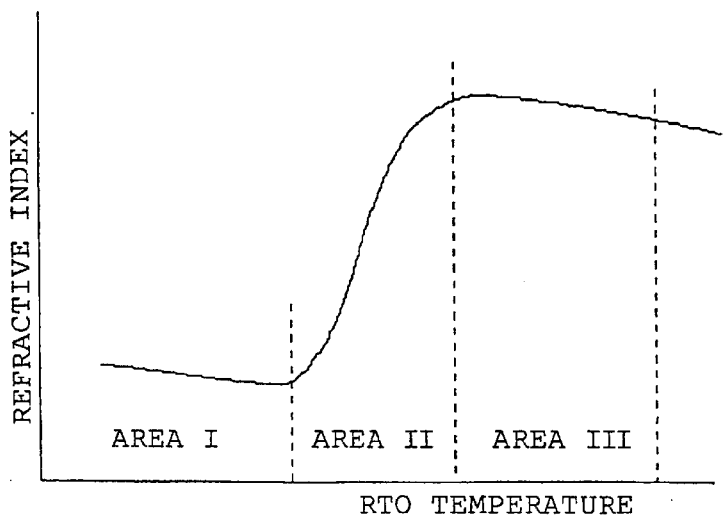
Figure 4:
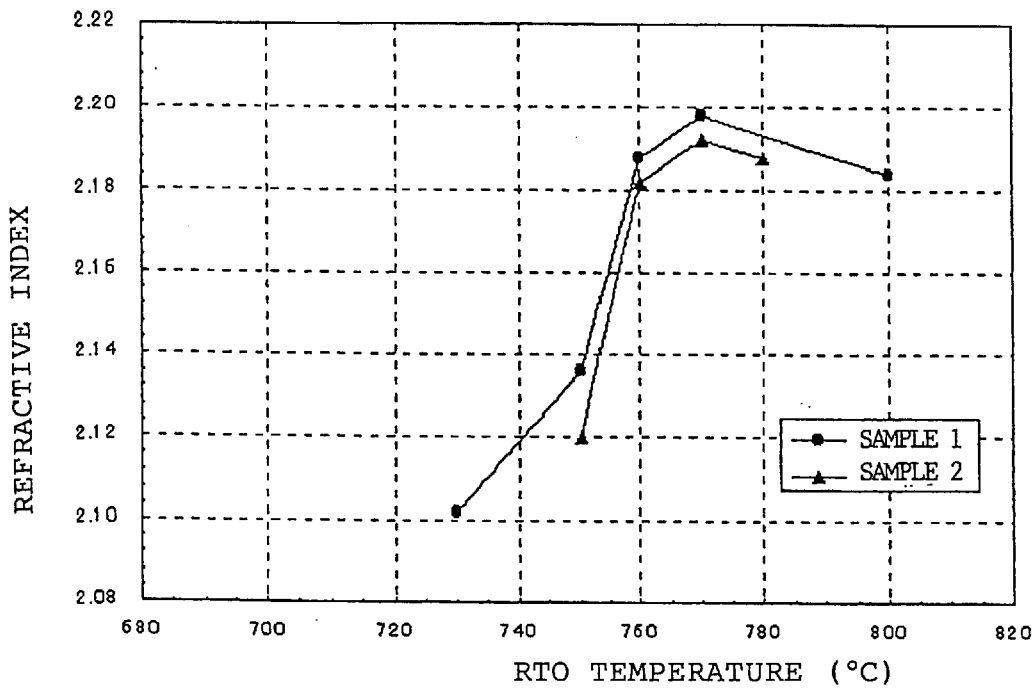
FIG. 4 shows measurement results that were obtained using the method of appraising a dielectric film of the first working example of the present invention.

We first refer to FIGS. 1 to 4 to explain the method of appraising dielectric films as the first working example of the present invention. FIG. 1 is a sectional view showing the method of fabricating an appraisal sample of a dielectric film, and FIG. 2 is a sectional view showing examples of constructions that can be appraised in this appraisal method. In addition, FIG. 3 shows the principles of the appraisal method of this working example; FIG. 3A showing the correlation between heat treatment temperature (RTO temperature) and the refractive index of dielectric film, FIG. 3B showing the correlation between the heat treatment temperature and the film thickness of the interface layer (silicon oxide film) that is formed at the silicon wafer interface, and FIG. 3C showing the correlation between the heat treatment temperature and the refractive index of the entirety of laminated films that includes a dielectric film and the interface layer. In addition, FIG. 4 shows the effect of this working example, and shows the correlation between RTO (Rapid Thermal Oxidation) temperature and the refractive index that was obtained from a sample that was actually produced.

Figure 1A:
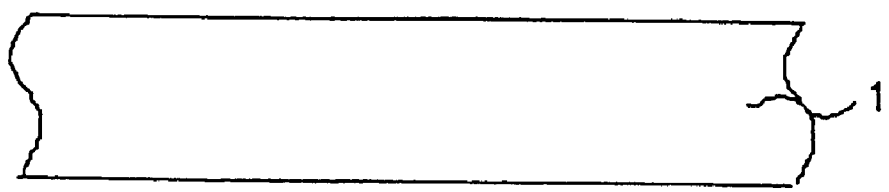
FIGS. 1A, 1B, and 1C are sectional views showing the method of producing samples used in appraising a dielectric film according to the first working example.
Figure 1B:
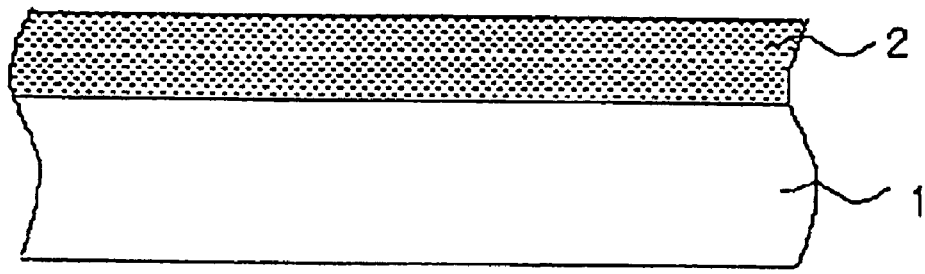

Referring now to FIG. 1, the method of fabricating the dielectric film, sample of this working example is first explained. As shown in FIGS. 1A and 1B, a substrate such as silicon wafer 1 on which dielectric films are to be grown is first prepared, following which a dielectric film such as tantalum pentoxide film 2 is grown on the substrate. The wafer on which the dielectric film is grown is not limited to a silicon wafer and may be any material that does not present an obstacle when measuring the refractive index, but silicon wafer 1 is used in this case because the appraisal of the dielectric film that is grown as the DRAM capacitors is the main object in the present invention. In addition, the dielectric film that is grown is not limited to tantalum pentoxide film 2 and any film may be used in which crystallinity is changed (for example, changed from amorphous to crystalline) by a heat treatment such as an oxidation treatment, other possible choices being yttrium oxide ($Y_2O_3$) and hafnium dioxide ($HfO_2$), which were used in the example of the prior art. Further, any method such as a sputtering method or a CVD method may be employed as the method of growing tantalum pentoxide film 2. In this case, a CVD method is used and tantalum pentoxide film 2 is grown to a film thickness of approximately 10 nm.

Figure 1C:
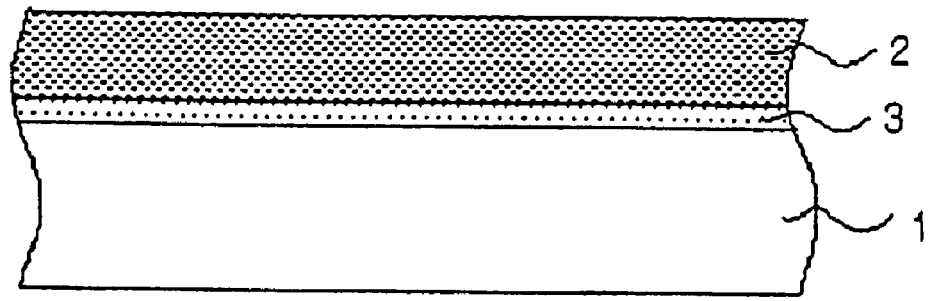

Next, as shown in FIG. 1C, the silicon wafer 1 on which tantalum pentoxide film 2 is formed is subjected to a heat treatment such as RTO. The heat treatment may be a lamp heat treatment in an oxygen atmosphere, treatment by an oxygen plasma, or irradiation by ultraviolet light in an ozone gas atmosphere. This RTO treatment both improves the crystallinity of tantalum pentoxide film 2 and causes oxygen atoms to penetrate tantalum pentoxide film 2 and react with underlying silicon wafer 1 to form silicon oxide film 3 at the interface of silicon wafer 1.

The sample that has been thus formed is used to measure the refractive index of the dielectric films on silicon wafer 1. Various methods exist for measuring the refractive index, but one typical method employs a spectral ellipsometer whereby polarized light is irradiated onto the object of measurement and the film thickness and refractive index of a thin film are measured based on the change in the state of polarization of the reflected light. Ellipsometry can be broadly divided between the extinction method and the rotational analyzer method. The extinction method involves using a compensator to convert elliptically polarized light that has been reflected to linearly polarized light and then finding the polarization parameters. The rotational analyzer method involves direct measurement of the polarized state of reflected light to find the polarization parameters. Although a method is described in the following explanation in which an ellipsometer is used to measure the refractive index of a dielectric film, other methods that allow measurement without causing damage may be employed as the method of measuring the refractive index.

FIG. 3A shows the change in refractive index of only tantalum pentoxide film 2 as the RTO treatment temperature is changed. As shown in FIG. 3A, tantalum pentoxide film 2 can be divided between three states according to the range of the RTO temperature (from area I to area III). Specifically, in area I, the heat energy is low because the RTO temperature is low and the crystallinity of tantalum pentoxide film 2 does not change. In area II, as the RTO temperature is gradually raised, tantalum pentoxide film 2 both gradually changes from an amorphous state to a crystalline state and oxygen atoms enter vacancies in tantalum pentoxide film 2. Then, in area III, the crystallization of tantalum pentoxide film 2 reaches completion in which crystallinity is not further improved despite further increase in the RTO temperature.

This change in refractive index in a dielectric film such as tantalum pentoxide film 2 takes place because, during the growth of oxides such as tantalum pentoxide by a method such as CVD, oxygen atoms easily escape during formation of the film and the film is in an amorphous state having poor crystallinity. When tantalum pentoxide film 2 is crystallized by an RTO treatment, oxygen atoms fill the vacancies of tantalum pentoxide film 2 and thus cause an increase in density, whereby the refractive index increases.

In contrast, the film thickness of silicon oxide film 3 that is formed below tantalum pentoxide film 2 changes as shown in FIG. 3B. Specifically, as the RTO temperature rises, the energy of oxygen atoms increases, the number of oxygen atoms that penetrate tantalum pentoxide film 2 and reach silicon wafer 1 increases, and the film thickness of silicon oxide film 3 that grows at the interface of silicon wafer 1 gradually increases.

The refractive index of the laminated films in which this tantalum pentoxide film 2 and silicon oxide film 3 are combined is a curve having a minimum value and a maximum value as shown in FIG. 3C. Specifically, the film quality of tantalum pentoxide film 2 in area I is unimproved and the refractive index of tantalum pentoxide film 2 alone is therefore unchanged at approximately 2.19, but the film thickness of silicon oxide film 3, which has a refractive index of 1.46 that is much smaller than that of tantalum pentoxide film 2, gradually increases. As a result, the refractive index of the entirety of the laminated films gradually decreases to reach a minimum value on the right side of area I.

Then, in area II, while the film thickness of silicon oxide film 3, which has a low refractive index, continues to gradually increase, the refractive index of tantalum pentoxide film 2 rises abruptly from approximately 2.19 to approximately 2.23 and the refractive index of the entirety of laminated films therefore increases rapidly. In area III, the refractive index of tantalum pentoxide again becomes a fixed value as in area I at approximately 2.23, but the increase in the film thickness of silicon oxide film 3 causes the refractive index of the entirety of laminated films to gradually decrease, with the value reaching a maximum on the left side of area III. This characteristic, in which the refractive index of the entirety of these laminated films changes with respect to the RTO temperature with inflection points was discovered by the inventors of the present invention.

When fabricating a semiconductor memory device such as DRAM, it is important that the capacitance of capacitors, i.e., the relative dielectric constant of the dielectric film, be reliably set to a high value. The desired refractive index, i.e., the desired relative dielectric constant, cannot be obtained if the temperature of the RTO process becomes excessively low. If, on the other hand, the temperature of the RTO process becomes excessively high, there is the concern that the diffusion layer that underlies the capacitors will extend, that impurities will diffuse into unwanted areas and thus alter the characteristics of transistors, and that the growth of silicon oxide film 3 will cause the refractive index to decrease. Accordingly, when fabricating DRAM, the RTO process must be performed in the vicinity of the maximum point at which the refractive index of the laminated films that include tantalum pentoxide film 2 reaches a maximum.

As a means of measuring the effect of the heat treatment following the RTO process in the prior art, a method was conventionally used in which the crystallinity of tantalum pentoxide film 2 itself was measured by an x-ray diffraction method. However, the results that were obtained by x-ray diffraction provide information for only tantalum pentoxide film 2, which is the uppermost layer on the wafer, and, since crystallinity does not change with changes in temperature when the RTO temperature enters area III as shown in FIG. 3A, this method cannot accurately determine the border between area II and area III.

Moreover, as described in the foregoing explanation, the capacitance of the capacitors of DRAM varies with the entirety of laminated films that includes silicon oxide film 3 at the interface of silicon wafer 1, and not with only tantalum pentoxide film 2, which is the uppermost layer. Accordingly, although the entirety of laminated films must be appraised to accurately predict the capacitance of the capacitors, a method such as the x-ray diffraction method of the prior art appraises only the crystallinity of tantalum pentoxide film 2, which is the uppermost layer. The method of the prior art was therefore incapable of estimating the capacitance of the DRAM as a finished product, and an accurate value could only be obtained by appraising the finished product.

In contrast, the method of appraising a dielectric film of this working example takes advantage of the fact that the refractive index of the dielectric films changes with respect to the RTO temperature as a curve having points of inflection as shown in FIG. 3C and thus can estimate the capacitance of the capacitors by measuring the refractive index by means of, for example, an ellipsometer without causing damage. This method enables measurement of the refractive index of the entirety of laminated films that includes not only tantalum pentoxide film 2, which is the uppermost layer, but also underlying silicon oxide film 3, and the method therefore not only enables easy and accurate estimation of the capacitors of the final product but also enables a shorter time for measurement than the x-ray diffraction method.

FIG. 4 shows the results of measuring refractive index by an ellipsometer after carrying out an RTO process in which temperature was varied for two samples that were separately formed in the method shown in FIG. 1. A slight difference in the film thickness of tantalum pentoxide film 2 in sample 1 and sample 2 of FIG. 4 results in the vertical shift shown in the figure. As for the correlation between the RTO temperature and refractive indices, however, the two samples are in accordance in that the refractive index tends to gradually decrease, particularly after reaching a maximum value at a temperature of 770° C. The refractive index of the entirety of laminated films that includes tantalum pentoxide film 2 can therefore be appraised with good reproducibility in the method of appraisal of this working example, and the temperature can be accurately adjusted to maximize the capacitance of capacitors in the finished product.

Although the above-described working example was described regarding a construction in which silicon oxide film 3 and tantalum pentoxide film 2 are laminated on a silicon wafer 1 as the measurement sample, the present invention is not limited to the above-described working example and can be applied to any dielectric film or laminated film in which crystallinity is changed by a heat treatment.

The present invention can also be used in a construction such as shown in FIG. 2A that includes silicon nitride film 4 that is grown between silicon wafer 1 and tantalum pentoxide film 2 by, for example, an RTN (Rapid Thermal Nitridation) method; in a construction such as shown in FIG. 2B that includes polysilicon 5 between silicon wafer 1 and tantalum pentoxide film 2; or in a construction such as shown in FIG. 2C that includes both polysilicon 5 and silicon nitride film 4. Although a silicon nitride film typically does not transmit oxygen, a thin silicon nitride film results in weak oxide resistance and allows a silicon oxide film to grow at the interface of silicon wafer 1, and the present invention can therefore be used in the construction shown in FIG. 2 that includes a silicon oxide film at the interface of silicon wafer 1.

Second Working Example

Figure 5:
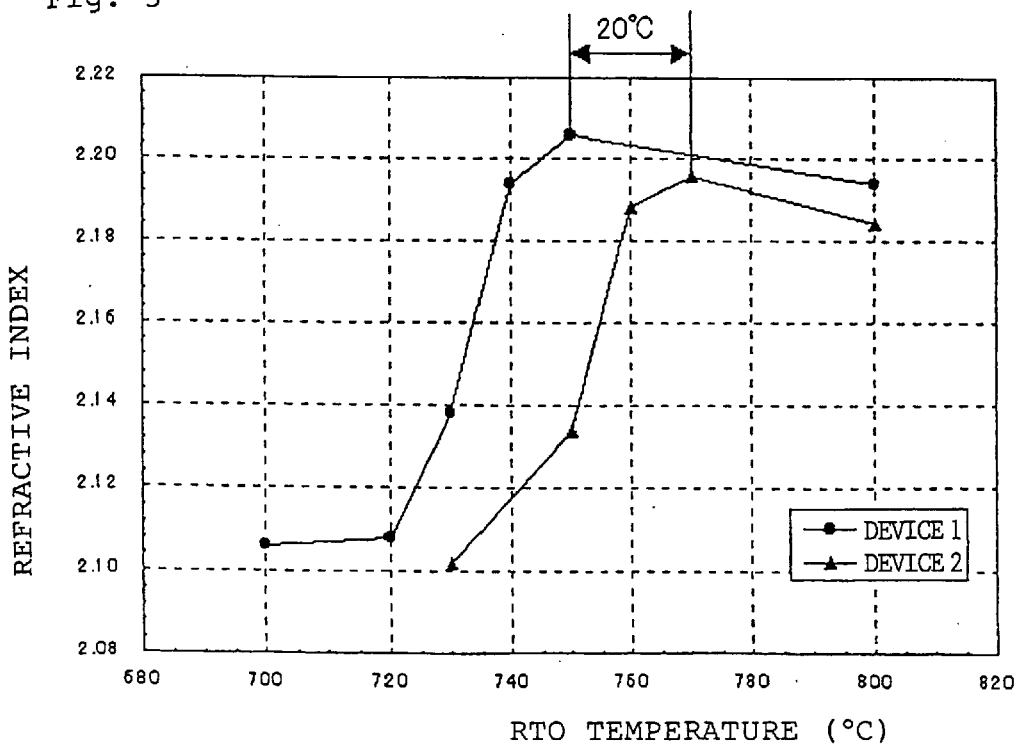
FIG. 5 shows measurement results that were obtained using the method of appraising a dielectric film of the second working example of the present invention.
Figure 6:
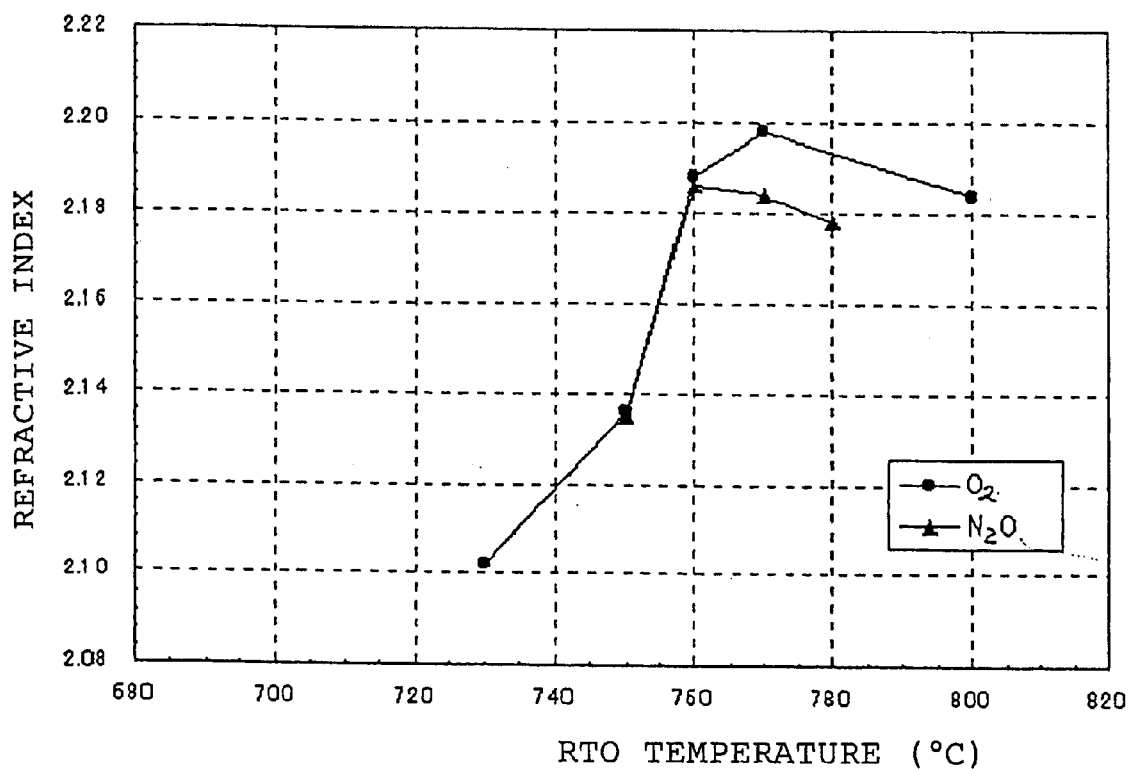
FIG. 6 shows measurement results that differ from FIG. 5 that were obtained using the method of appraising a dielectric film of the second working example of the present invention.

We now refer to FIGS. 5 and 6 to explain, as the second working example of the present invention, a method of calibrating a semiconductor fabrication device that takes advantage of the above-described method of appraising a dielectric film. FIG. 5 shows the correlation between the RTO temperature (the set value of the devices) in differing RTO devices and the refractive index of laminated films that include a tantalum pentoxide film; and FIG. 6 shows the correlation between RTO temperature and the refractive index of laminated films that include a tantalum pentoxide film when varying the type of gas that is introduced to the device. This working example uses the previously described method of appraising a dielectric film of the first working example to monitor and calibrate a semiconductor fabrication device such as an RTO device.

As described in the foregoing explanation, a dielectric film such as a tantalum pentoxide film that is formed by a CVD method must undergo a heat treatment to improve its crystallinity. The crystallinity of a thin film following heat treatment, i.e., the refractive index, depends largely on the temperature of the heat treatment device, and the temperature range that maximizes the refractive index of the entirety of the laminated films that include the interface layer is restricted to a narrow range. In addition, the heat treatment temperature must be set as low as possible so as not to alter the characteristics of components such as transistors that have been formed in underlying layers in the fabrication steps of a semiconductor memory device. The temperature of the heat treatment must therefore be accurately controlled, but a divergence may occur between the set temperature of the heat treatment device and the actual treatment temperature.

When a lamp annealing device is used as an oxidation treatment device, for example, the temperature value that is indicated in the device is monitored by a temperature sensor that is provided inside the device, but the set temperature of the device will not precisely match the actual temperature because the measurement value of the temperature sensor will vary slightly according to the position at which the temperature sensor is placed.

When this type of heating device is used in fabricating a semiconductor memory device, the correlation between the temperature that is set beforehand and the actual temperature inside the device must be checked and the set temperature then adjusted based on the correlative data. However, in a device that includes the above-described heating mechanism, in addition to the divergence of temperature of that particular device, the temperature may also fluctuate due to the influence of changes in the characteristics of the heating portion such as the lamp that occur as the device operates or variations in the reflection of the light of the lamp or convection of heat that are caused by the type, number, and arrangement of samples that are placed inside the apparatus.

Even though the set temperature of a device remains the same during repetition of the heating process, the actual treatment temperature will in some cases fall below the set temperature such that the crystallinity of the dielectric film is not adequately improved, or in other cases, rise above the set temperature such that the characteristics of components such as transistors are altered. Since no method existed for easily appraising such shifts in temperature in the prior art, the suitability of the set temperature in the heat treatment could be judged only by actually completing a semiconductor memory device and then appraising the performance of the device, and this requirement greatly reduced the yield of the semiconductor memory device.

In the present working example, correlative data of the temperature and refractive index are obtained at the time of periodic calibration and maintenance, and variation in the treatment temperature between devices is adjusted based on this data. Alternatively, each time a heating treatment is performed on a semiconductor memory device such as DRAM, a portion of the product wafer is used to check the refractive index of the dielectric film without causing damage, and the measured value is then compared with correlative data that have been measured beforehand. Comparison results are also be fed back from time to time to perform temperature calibration so as to limit fluctuations that occur in a device over time and constantly keep the state of the fabrication device uniform.

Specifically, the correlation between the refractive index of dielectric films and the RTO set temperature for device 1 and device 2 is checked as shown in FIG. 5, and these data are-used to adjust for divergence in temperature between the two devices or for divergence of the actual treatment temperature from the set temperature. Then, each time a heat treatment is performed, portions of the semiconductor device (points at which a dielectric film is grown on the silicon wafer) are used to measure the refractive index by means of an ellipsometer, and these measured values are then compared with the above-described data to determine whether or not the set temperature is appropriate. At this time, when it is judged that error has occurred between the set temperature of a device and the actual temperature, correlative data of the RTO temperature and refractive index are again obtained for that device and temperature calibration is carried out.

This type of method eliminates the need for the separate production of a wafer for x-ray diffraction measurement and time-consuming measurements and therefore enables appropriate and accurate calibration of a semiconductor fabrication device such as a heat treatment device. This method can also be applied for a case in which different gasses are used in the same device.

As an example, when O2 and N2O are used as the gas types, the refractive index of laminated films that include tantalum pentoxide film 2 is as shown in FIG. 6, and reference to these data enables adjustment of the mixture ratio of the gasses when a film is being grown.

Third Working Example

Figure 7A:
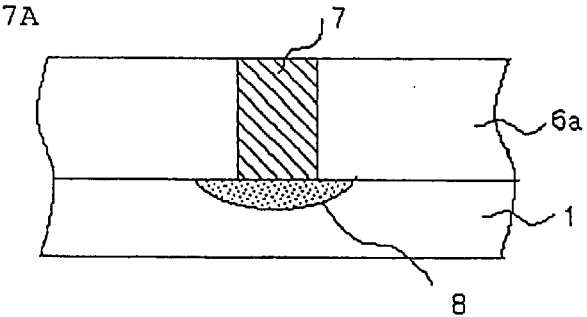
FIGS. 7A, 7B, 7C, and 7D are sectional views of steps and give a schematic representation of a portion of the DRAM fabrication method according to the third working example of the present invention.
Figure 7B:
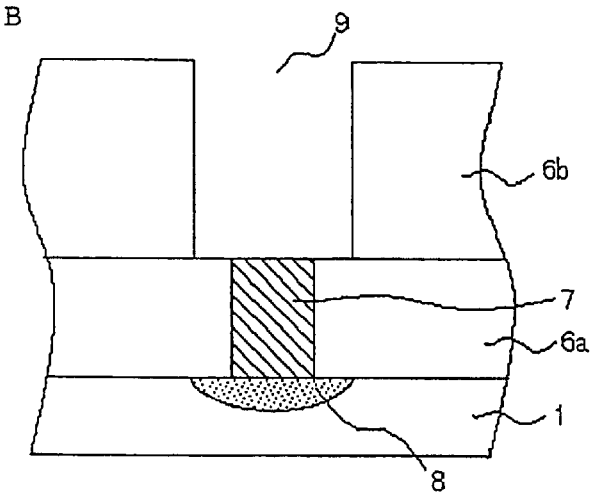
Figure 7C:
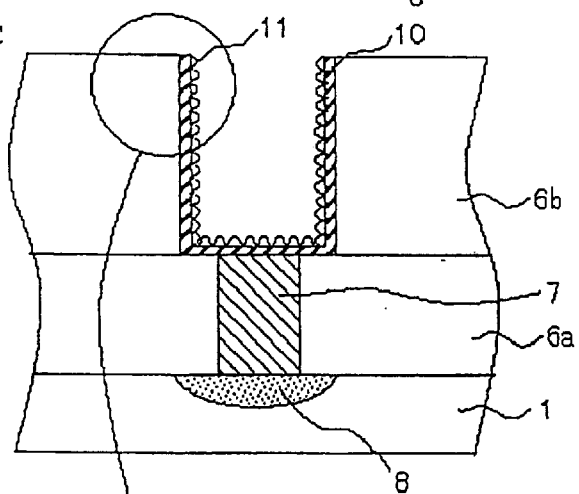
Figure 7D:
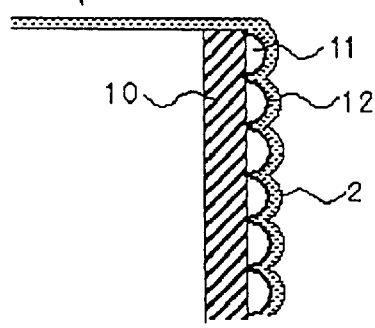
Figure 8A:
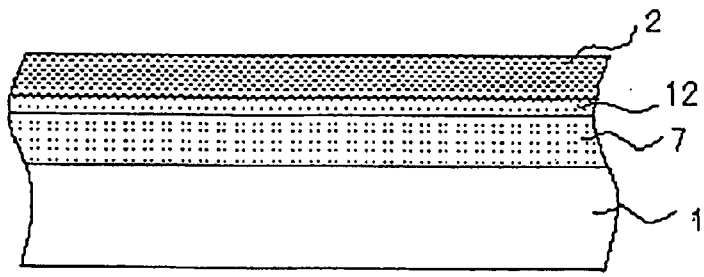
FIGS. 8A and 8B are sectional views showing locations for appraising a dielectric film according to the third working example of the present invention.
Figure 8B:
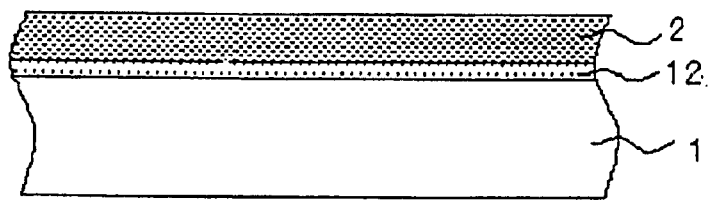
Figure 8C:
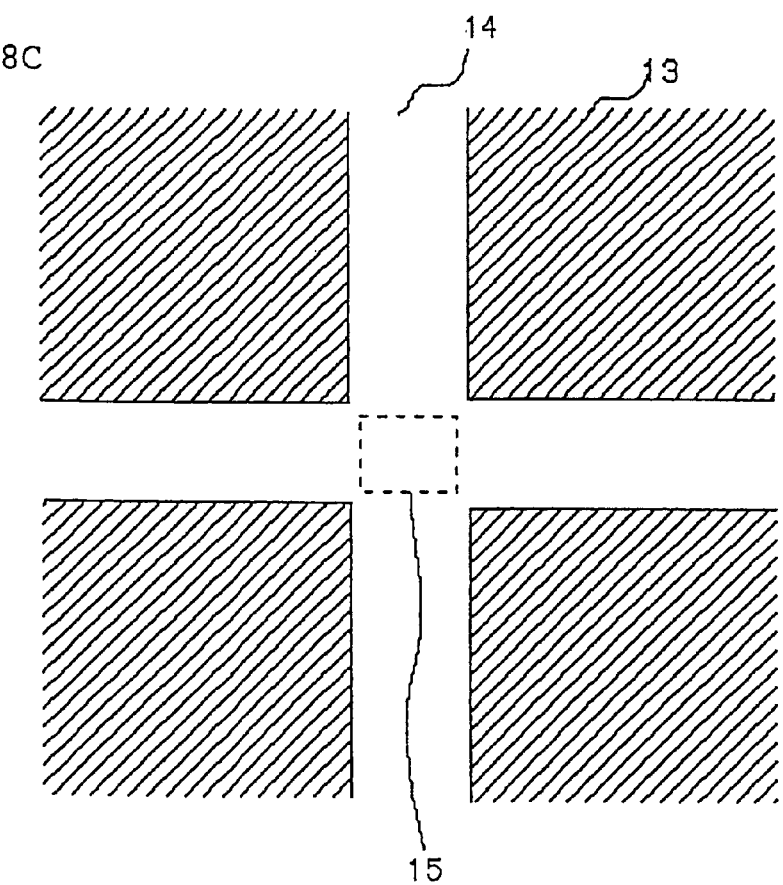
FIG. 8C is a plan view of the scribe line area of the same working example.
Figure 9:
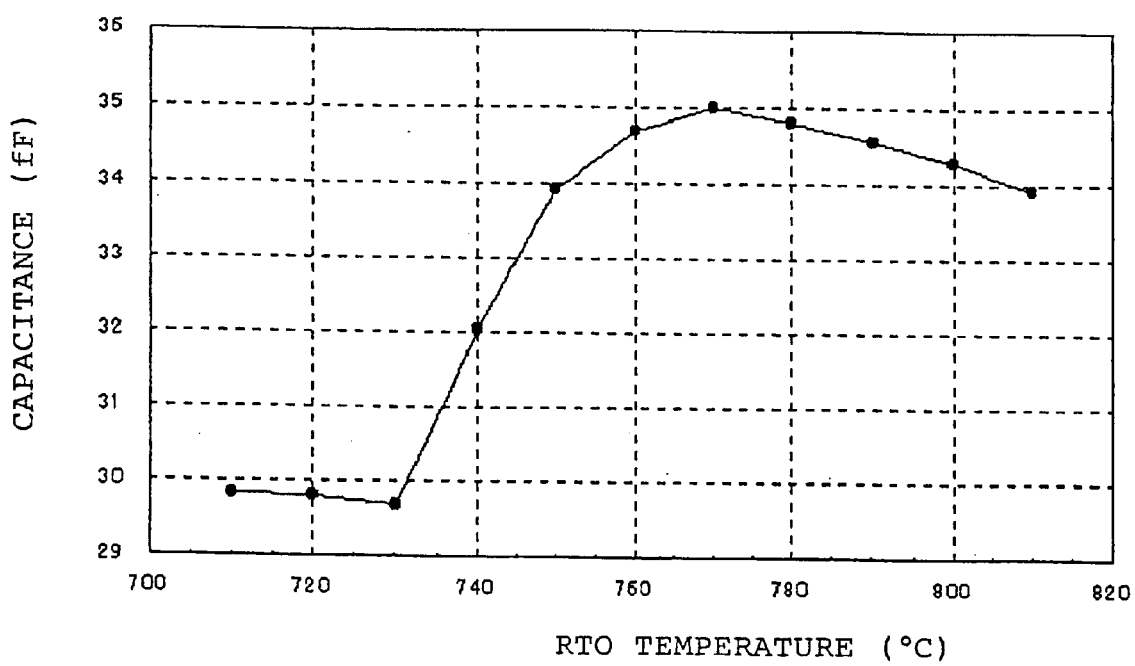
FIG. 9 shows measurement results that were obtained using the method. of appraising a dielectric film of the third working ex-ample of the present invention.

We now refer to FIGS. 7 to 9 to explain a method of fabricating DRAM as the third working example of the present invention. FIG. 7 is a sectional view that gives a schematic representation of a portion of the steps in the DRAM fabrication method. FIG. 8 shows the locations for measurement of the refractive index on a wafer product, FIGS. 8A and 8B showing sectional views and FIG. 8C showing a plan view of the scribe line area. FIG. 9 shows the effect of the present working example and shows the correlation between RTO temperature and the capacitance of the DRAM. The present working example regards a method of fabricating DRAM in which a step is introduced for using a wafer product following formation of a dielectric film to measure the refractive index of the dielectric film.

Explanation first regards the method of fabricating DRAM. Since components such as transistors are fabricated by ordinary methods, explanation regarding these components is omitted in this explanation. Explanation is presented with reference to FIG. 7 from the step of forming capacitors, this step being pertinent to the method of appraising the dielectric film. As shown in FIG. 7A, a plasma CVD method is used to form an insulation film such as silicon oxide film 6a on silicon wafer 1 to a film thickness of approximately 1 $\mu$m. A contact hole is next opened by known photolithographic and etching techniques, and n+-diffusion layer 8 is then formed by ion implantation. Polysilicon doped with, for example, phosphorus is then grown and etched back to bury polysilicon 7 inside the contact hole, thereby forming a contact hole.

As shown in, FIG. 7B, a plasma CVD method is used to grow an insulation film such as silicon oxide film 6b to a film thickness of approximately 2 $\mu$m, following which known photolithographic and etching techniques are employed to etch the portion of silicon oxide film 6b that overlies the contact and form capacitor portion 9 of cylindrical structure.

HSG is next formed to increase the surface area in capacitor portion 9 as shown in FIG. 7C. Specifically, amorphous silicon doped with, for example, phosphorus, is grown over the entire substrate surface to a film thickness of approximately 40 $\mu$m, and an etching method is then used to remove only the amorphous silicon on the surface to form amorphous silicon 10 only on the inner walls of the cylinder structure. Heat is then applied to a temperature sufficient to bring about crystallization of amorphous silicon 10, whereby silicon atoms are diffused with high mobility and collide with each other to form crystal nuclei. Crystallization progresses in the direction of depth from the points of formation of the crystal nuclei to produce hemispherical crystal grains having a diameter of several tens of nanometers, thereby forming an HSG structure.

Next, as shown in FIG. 7D, an RTN method is employed to form silicon nitride film 12 on the surface of the HSG structure. A CVD method is then used to grow tantalum pentoxide film 2 to a film thickness of approximately 8 nm, following which tantalum pentoxide film 2 is subjected to an oxidation treatment by RTO to improve the crystallinity of tantalum pentoxide film 2. At this time, RTO is carried out for one minute under the conditions of, for example, atmospheric pressure and an oxygen flow rate of 5 SLM to enable improvement of the crystallinity of tantalum pentoxide film 2 such that the refractive index of the laminated films that include tantalum pentoxide film 2 reaches a maximum.

A portion of the DRAM wafer is then used to measure the refractive index to determine the adequacy of the RTO process. Measurement by an ellipsometer normally requires a size of 50 $\mu$m×50 $\mu$m, and a pattern for measurement purposes can therefore be formed in chip area 13 of the DRAM. However, the use of scribe line 14 as shown in FIG. 8C allows appraisal without increasing the area of the chip. At this time, a section of the measurement area is preferably a structure in which polysilicon 7, silicon nitride film 12, and tantalum pentoxide film 2 are laminated in three layers on silicon wafer 1 as shown in FIG. 8A or a structure in which silicon nitride film 12 and tantalum pentoxide film 2 are laminated in two layers on silicon wafer 1 as shown in FIG. 8B.

The refractive index of the dielectric films of the laminated structure is then measured to enable an accurate prediction of the capacitance of the capacitors of the DRAM.

The occurrence of problems can be suppressed to a minimum by taking measures such as supplementing the RTO process if the RTO process is inadequate or adjusting the set temperature of the device if there is a divergence between the set temperature and the actual treatment temperature.

The correlation between the RTO temperature and the capacitance per cell (fF) of DRAM that has been formed by the method of this working example is as shown in FIG. 9. These data can be prepared in advance to enable accurate prediction of the cell capacitance of the DRAM based on the refractive index following the RTO process even before completion of the DRAM.

As described in the foregoing explanation, the measurement of refractive index following heat treatment of a dielectric film according to the present invention enables measurement of not only the crystallinity of the dielectric film of the uppermost layer but the refractive index of the entirety of the laminated films including the film that forms at the interface, thereby enabling the easy and reliable estimate of the capacitance of capacitors even at a stage midway through fabrication.

In addition, the use of refractive index to appraise the crystallinity of a dielectric film enables measurement without causing damage, eliminates the need to separately fabricate a sample for measurement purposes, and enables a reduction of the steps required for measurement.

Using the method of the present invention, measurement of data in advance that correlate refractive indices with RTO temperatures for each device enables detection of discrepancies in the treatment temperature between devices and fluctuations over time in a device, and in addition, feedback of the results of comparing these correlative data with data of the refractive indices that are measured following heat treatment allows semiconductor fabrication devices to be kept in a constant uniform state.

Finally, the use of a portion (such as a scribe line) of a semiconductor memory device such as DRAM to measure refractive index enables the measurement of the refractive index of a dielectric film that has been grown on an actual wafer product and enables the accurate prediction of the cell capacitance of a semiconductor memory device.

It is to be understood, however, that although the characteristics and advantages of the present invention have been set forth in the foregoing description, the disclosure is illustrative only, and changes may be made in the arrangement of the parts within the scope of the appended claims.

What is claimed is:

1. A method of appraising dielectric films that are deposited on a substrate; wherein at least one of change in the crystallinity and change in the relative dielectric constant of said dielectric films before and after a heat treatment that is performed in an atmosphere that contains oxygen is appraised by measuring the refractive index of said dielectric films.

2. A method of appraising dielectric films according to claim 1, wherein said dielectric films are composed of laminated films of a plurality of dielectric films each having different relative dielectric constants, and the refractive index of said laminated films is measured to estimate the relative dielectric constant of the entirety of said plurality of dielectric films.

3. A method of appraising dielectric films according to claim 1, wherein said plurality of dielectric films includes a dielectric film in which crystallinity is changed by said heat treatment, and a dielectric film in which film thickness is changed by said heat treatment.

4. A method of appraising dielectric films according to claim 1, wherein said dielectric films include any one of a tantalum pentoxide film, an yttrium oxide film, and a hafnium oxide film.

5. A method of appraising a dielectric films according to claim 1, wherein said dielectric films are formed on silicon or a polysilicon film either in direct contact with said silicon or polysilicon film or with a silicon oxide film or silicon nitride film interposed.

6. A method of appraising dielectric films according to claim 5, wherein
a silicon oxide film is formed by said heat treatment at the interface of said silicon or said polysilicon film.

7. A method of appraising dielectric films according to claim 1, wherein said refractive index is measured by a spectral ellipsometer.

8. A method of calibrating the temperature of a heat treatment device that subjects a dielectric film that has been deposited on a substrate to a heat treatment in an atmosphere that contains oxygen, wherein:
correlative data of temperatures of said heat treatment and refractive indices of said dielectric film that has undergone heat treatment at said temperatures are used to correct divergence between the set temperature of said heat treatment device and the actual treatment temperature.

9. A method of calibrating temperature of heat treatment devices according to claim 8, wherein:
correlative data of the refractive indices of said dielectric films and temperatures of said heat treatment that are obtained for each individual device of a plurality of said heat treatment devices are consulted to correct temperature differences between said plurality of heat treatment devices.

10. A method of calibrating temperature of a heat treatment device according to claim 8, wherein correlative data of the temperatures of said heat treatment and the refractive indices of said dielectric film are obtained in advance for said heat treatment device, and the correlative data are then compared with data of the refractive index of said dielectric film that is subsequently subjected to treatment to correct for temperature fluctuations of said heat treatment device that occurs over time.

11. A method of calibrating temperature of a heat treatment device according to claim 8, wherein said dielectric film is composed of laminated films that include a dielectric film in which said heat treatment causes a change in crystallinity, and a dielectric film in which said heat treatment causes a change in film thickness.

12. A method of calibrating temperature of a heat treatment device according to claim 8, wherein said dielectric film includes any one of a tantalum pentoxide film, a yttrium oxide film, and a hafnium oxide film.

13. A method of calibrating temperature of a heat treatment device according to claim 8, wherein said refractive index is measured by a spectral ellipsometer.

14. A method of fabricating a semiconductor memory device that includes a step of carrying out a heat treatment in an atmosphere that contains oxygen after forming a dielectric film in a capacitor; said step of subjecting said dielectric film to a heat treatment comprising:
using a portion of the substrate on which [said] semiconductor memory device is formed to measure the refractive index of said dielectric film after said heat treatment to appraise at least one of change in the crystallinity of said dielectric film and change in the relative dielectric constant of said dielectric film and thus estimate the capacitance of said capacitors after completion of said semiconductor memory device.

15. A method of fabricating a semiconductor memory device according to claim 14, wherein a scribe line of said semiconductor memory device is used to measure said refractive index.

16. A method of fabricating a semiconductor memory device according to claim 14, wherein:
said dielectric film is composed of laminated films of a plurality of dielectric films each having a different relative dielectric constant; and
the refractive index of said whole laminated films is measured to estimate the relative dielectric constant of the entirety of said plurality of dielectric films.

17. A method of fabricating a semiconductor memory device according to claim 14, wherein said dielectric films include any one of a tantalum pentoxide film, a yttrium oxide film, and a hafnium oxide film.

18. A method of fabricating a semiconductor memory device according to claim 17, wherein
said dielectric film is formed on a silicon or polysilicon film either in direct contact with said silicon or polysilicon film or with a silicon oxide film or silicon nitride film interposed.

19. A method of fabricating a semiconductor memory device according to claim 18, wherein
a silicon oxide film is formed by said heat treatment at the interface of said silicon or said polysilicon film.

* * * * *